United States Patent [19]
Miyazaki et al.

[11] Patent Number: 5,726,291
[45] Date of Patent: Mar. 10, 1998

[54] AMYLASE INHIBITORS

[75] Inventors: Toshiyuki Miyazaki; Toshihisa Morimoto, both of Ohimachi; Ryuji Murayama, Hyogo-ken, all of Japan

[73] Assignees: Nisshin Flour Milling Co., Ltd., Tokyo; Nagata Sangyo Co., Ltd., Hyogo-ken, both of Japan

[21] Appl. No.: 782,176

[22] Filed: Jan. 14, 1997

[30] Foreign Application Priority Data

Jan. 18, 1996 [JP] Japan ................... 8-023446

[51] Int. Cl.$^6$ ............... C07K 3/02; C07K 3/24; C07K 15/10; A61K 38/16
[52] U.S. Cl. ............... 530/375; 530/374; 514/2; 514/8; 514/12
[58] Field of Search ............... 530/374, 375, 530/416, 419; 514/2, 8, 12

[56] References Cited

U.S. PATENT DOCUMENTS

| | | | |
|---|---|---|---|
| 5,332,803 | 7/1994 | Miyazaki et al. | 530/375 |
| 5,440,019 | 8/1995 | Miyazaki et al. | 530/374 |
| 5,444,046 | 8/1995 | Miyazaki et al. | 514/12 |

FOREIGN PATENT DOCUMENTS

| | | |
|---|---|---|
| 46-1833 | 10/1971 | Japan . |
| 61-171431 | 8/1986 | Japan . |
| 5-301898 | 11/1993 | Japan . |
| 7-41499 | 2/1995 | Japan . |
| 7-48268 | 2/1995 | Japan . |
| 7-48400 | 2/1995 | Japan . |

OTHER PUBLICATIONS

W. Puls, et al., "Influence of an α–Amylase Inhibitor (Bay d 7791) on Blood Glucose, Serum Insulin and NEFA in Starch Loading Tests in Rats, Dogs and Man", Diabetologia, vol. 9, (1973), pp. 97–101.

Rosa Sanchez–Monge, et al., "New Dimeric Inhibitor of Heterologous α–amylases Encoded by a Duplicated Gene in the Short Arm of Chromosome 3B of Wheat (*Triticum aestivum* L.)", Eur. J. Biochem, vol. 183, (1989), pp. 37–40.

Nizar Kashlan, et al., "The Complete Amino Acid Sequence of a Major Wheat Protein Inhibitor of α–Amylase", Phytochemistry, vol. 20, No. 8, (1981), pp. 1781–1784.

Baruch J. Davis, "Disc Electrophoresis—II Method and Application to Human Serum Proteins", Annals New York Academy of Sciences, vol. 121, (1964), pp. 404–427.

K. Maeda, et al., "Complete Amino Acid Sequence of an α–Amylase Inhibitor in Wheat Kernel", Biochimica et Biophysica Acta, vol. 743, (1983), pp. 52–57.

*Primary Examiner*—Cecilia J. Tsang
*Assistant Examiner*—Michael Borin
*Attorney, Agent, or Firm*—Oblon, Spivak, McClelland, Maier & Neustadt, P.C.

[57] ABSTRACT

An amylase inhibitor consisting of a protein constructed of 244 amino acid residues having two subunits each identified as SEQ ID NO:1, in which a single band is observed at a mobility of 0.26 by polyacrylamide gel electrophoresis, and having a high inhibitory activity against human pancreatic α-amylase to inhibit an increase in blood glucose level, control an insulin secretion or maintain the duration in a feeling of satiety for diet. The amylase inhibitor can be used alone or in combination with other known amylase inhibitors.

17 Claims, 1 Drawing Sheet

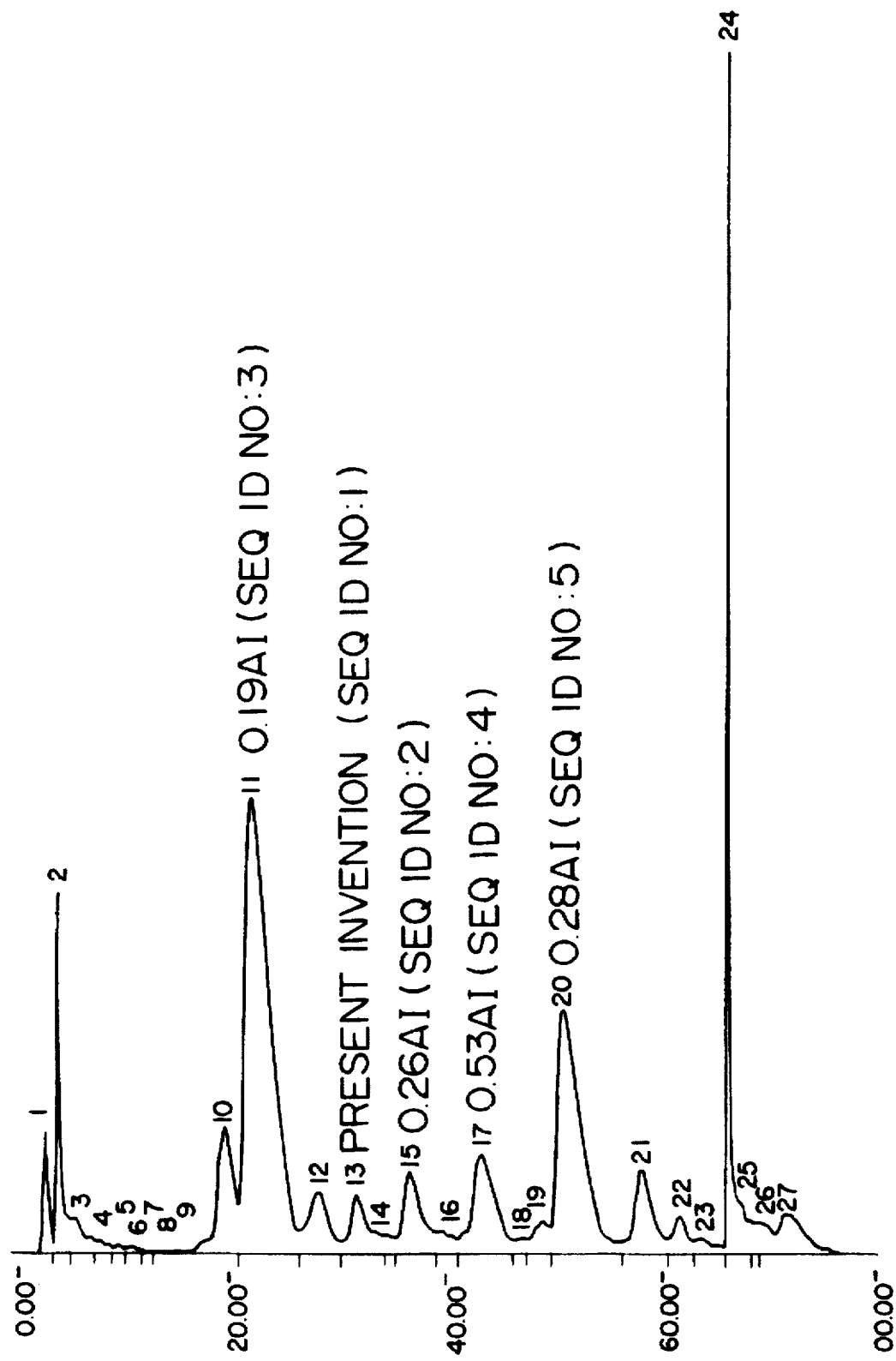

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 122 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Ser Gly Pro Trp Met Cys Tyr Pro Gly Tyr Ala Phe Lys Val Pro Ala
 1               5                  10                  15
Leu Pro Gly Cys Arg Pro Val Leu Lys Leu Gln Cys Asn Gly Ser Gln
                20                  25                  30
Val Pro Glu Ala Val Leu Arg Asp Cys Cys Gln Gln Leu Ala Asp Ile
                35                  40                  45
Ser Glu Trp Cys Arg Cys Gly Ala Leu Tyr Ser Met Leu Asp Ser Met
        50                  55                  60
Tyr Lys Glu His Gly Val Gln Glu Gly Gln Ala Gly Thr Gly Ala Phe
 65                 70                  75                  80
```

```
Pro  Ser  Cys  Arg  Arg  Glu  Val  Val  Lys  Leu  Thr  Ala  Ala  Ser  Ile  Thr
                    85                       90                      95

Ala  Val  Cys  Lys  Leu  Pro  Ile  Val  Ile  Asp  Ala  Ser  Gly  Asp  Gly  Ala
               100                      105                     110

Tyr  Val  Cys  Lys  Gly  Val  Ala  Ala  Tyr  Pro
               115                 120
```

( 2 ) INFORMATION FOR SEQ ID NO:2:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Ser  Gly  Pro  Trp  Met  Cys  Tyr  Pro  Gly  Tyr  Ala  Phe  Lys  Val  Pro  Ala
1                   5                        10                     15

Leu  Pro  Gly  Cys  Arg  Pro  Val  Leu  Lys  Leu  Gln  Cys  Asn  Gly  Ser  Gln
               20                       25                      30

Val  Pro  Glu  Ala  Val  Leu  Arg  Asp  Cys  Cys  Gln  Gln  Leu  Ala  Asp  Ile
               35                       40                      45

Ser  Glu  Trp  Cys  Arg  Cys  Gly  Ala  Leu  Tyr  Ser  Met  Leu  Asp  Ser  Met
          50                       55                      60

Tyr  Lys  Glu  His  Gly  Val  Gln  Glu  Gly  Gln  Ala  Gly  Thr  Gly  Ala  Phe
65                       70                      75                      80

Pro  Ser  Cys  Arg  Arg  Glu  Val  Val  Lys  Leu  Thr  Ala  Ala  Ser  Ile  Thr
                    85                       90                      95

Ala  Val  Cys  Lys  Leu  Pro  Ile  Val  Ile  Asp  Ala  Ser  Gly  Asp  Gly  Ala
               100                      105                     110

Tyr  Val  Cys  Lys  Gly  Val  Ala  Ala  Tyr  Pro  Asp  Ala
               115                 120
```

( 2 ) INFORMATION FOR SEQ ID NO:3:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Ser  Gly  Pro  Trp  Met  Cys  Tyr  Pro  Gly  Gln  Ala  Phe  Gln  Val  Pro  Ala
1                   5                        10                     15

Leu  Pro  Ala  Cys  Arg  Pro  Leu  Leu  Arg  Leu  Gln  Cys  Asn  Gly  Ser  Gln
               20                       25                      30

Val  Pro  Glu  Ala  Val  Leu  Arg  Asp  Cys  Cys  Gln  Gln  Leu  Ala  His  Ile
               35                       40                      45

Ser  Glu  Trp  Cys  Arg  Cys  Gly  Ala  Leu  Tyr  Ser  Met  Leu  Asp  Ser  Met
          50                       55                      60

Tyr  Lys  Glu  His  Gly  Ala  Gln  Glu  Gly  Gln  Ala  Gly  Thr  Gly  Ala  Phe
65                       70                      75                      80

Pro  Arg  Cys  Arg  Arg  Glu  Val  Val  Lys  Leu  Thr  Ala  Ala  Ser  Ile  Thr
                    85                       90                      95

Ala  Val  Cys  Arg  Leu  Pro  Ile  Val  Val  Asp  Ala  Ser  Gly  Asp  Gly  Ala
               100                      105                     110
```

```
        Tyr  Val  Cys  Lys  Asp  Val  Ala  Ala  Tyr  Pro  Asp  Ala
                  115                 120
```

( 2 ) INFORMATION FOR SEQ ID NO:4:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

```
Ser  Gly  Pro  Trp  Met  Cys  Tyr  Pro  Gly  Gln  Ala  Phe  Gln  Val  Pro  Ala
1                   5                        10                      15

Leu  Pro  Gly  Cys  Arg  Pro  Leu  Leu  Lys  Leu  Gln  Cys  Asn  Gly  Ser  Gln
               20                      25                      30

Val  Pro  Glu  Ala  Val  Leu  Arg  Asp  Cys  Cys  Gln  Gln  Leu  Ala  Asp  Ile
          35                      40                      45

Ser  Glu  Trp  Pro  Arg  Cys  Gly  Ala  Leu  Tyr  Ser  Met  Leu  Asp  Ser  Met
     50                      55                      60

Tyr  Lys  Glu  His  Gly  Val  Ser  Glu  Gly  Gln  Ala  Gly  Thr  Gly  Ala  Phe
65                       70                      75                      80

Pro  Ser  Cys  Arg  Arg  Glu  Val  Val  Lys  Leu  Thr  Ala  Ala  Ser  Ile  Thr
               85                      90                      95

Ala  Val  Cys  Arg  Leu  Pro  Ile  Val  Val  Asp  Ala  Ser  Gly  Asp  Gly  Ala
               100                     105                     110

Tyr  Val  Cys  Lys  Asp  Val  Ala  Ala  Tyr  Pro  Asp  Ala
               115                     120
```

( 2 ) INFORMATION FOR SEQ ID NO:5:

( i ) SEQUENCE CHARACTERISTICS:
        ( A ) LENGTH: 123 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

```
Ser  Gly  Pro  Trp  Ser  Trp  Cys  Asn  Pro  Ala  Thr  Gly  Tyr  Lys  Val  Ser
1                   5                        10                      15

Ala  Leu  Thr  Gly  Cys  Arg  Ala  Met  Val  Lys  Leu  Gln  Cys  Val  Gly  Ser
               20                      25                      30

Gln  Val  Pro  Glu  Ala  Val  Leu  Arg  Asp  Cys  Cys  Gln  Gln  Leu  Ala  Asp
          35                      40                      45

Ile  Asn  Asn  Glu  Trp  Cys  Arg  Cys  Gly  Asp  Leu  Ser  Ser  Met  Leu  Arg
     50                      55                      60

Ala  Val  Tyr  Gln  Glu  Leu  Gly  Val  Arg  Glu  Gly  Lys  Glu  Val  Leu  Pro
65                       70                      75                      80

Gly  Cys  Arg  Lys  Glu  Val  Met  Lys  Leu  Thr  Ala  Ala  Ser  Val  Pro  Glu
               85                      90                      95

Val  Cys  Lys  Val  Pro  Ile  Pro  Asn  Pro  Ser  Gly  Asp  Arg  Ala  Gly  Val
               100                     105                     110

Cys  Tyr  Gly  Asp  Trp  Cys  Ala  Tyr  Pro  Asp  Val
               115                     120
```

AMYLASE INHIBITORS

FIELD OF THE INVENTION

This invention relates to a new protein of wheat origin having a high inhibitory activity against human pancreatic α-amylase, an amylase inhibitor comprising the new protein as an active ingredient and the application of the amylase inhibitor as medicines and foods.

BACKGROUND OF THE INVENTION

Intake of excessive nutrients induces secretion of a larger amount of insulin to indirectly cause a loss of metabolic balance, thus leading to a reduction in glucose tolerating function (hyperglycemia), diabetes, hyperlipemia, arteriosclerosis, etc. Especially in diabetic patients, the insulin function is insufficient and the glucose tolerance is lowered. Consequently, the blood glucose level is remarkably increased after meals, thereby causing complications such as damages in blood capillary and arteriosclerosis. For the prevention and treatment of such diseases, it is effective to ingest foods or materials which can hardly induce an increase in blood glucose level. In this connection, the substances capable of inhibiting or preventing hydrolysis of starch into glucose have been desired. Further, overeating may be one of the causes inducing adult diseases such as obesity, hypertension, diabetes, cardiac diseases, etc.

From the above aspects, various studies have been made on the so-called amylase inhibitors which are effective in inhibiting the activity of amylase to hydrolyze starch to glucose. Amylase inhibitors of wheat origin are disclosed in Japanese Patent Kokai 46-1833 and 61-171431; Phytochemistry, Vol. 20, No. 8, pp. 1781–1784 (1981) and Eur. J. Biochem., 183, pp. 37–40 (1989).

The prior amylase inhibitors of wheat origin as mentioned above have a low or little inhibitory activity against human pancreatic α-amylase, which could not produce the effects as expected when orally given to humans, although they have some inhibitory activity against amylases derived from other animals than humans, and show a low inhibitory activity against decomposition of heated or cooked starch, especially, such as boiled rice. Therefore, there has been desired a highly active amylase inhibitor having a potent inhibitory activity against human pancreatic α-amylase, capable of effectively inhibiting an increase in blood glucose level and insulin secretion at a low dose level when orally administered, especially capable of effectively inhibiting hydrolysis of heated or cooked starch to glucose.

In Puls and Keup, "Diabetologia", 9, pp. 97–101 (1973), it is mentioned that an agent for inhibiting an increase in blood glucose level or insulin secretion may bring about an increased level of free fatty acid in blood. Such increased level of free fatty acids in blood may generally induce a feeling of hunger, which will readily lead to overeating. This results in offsetting the effect of inhibiting an increase in blood glucose level and the effect of inhibiting an insulin secretion, which will make it difficult to effectively treat or prevent the diseases such as diabetes.

Under these circumstances, we have made extensive studies on the amylase inhibitors of wheat origin and found industrially efficient processes for the preparation of amylase inhibitors having a high amylase inhibitory activity from the extract of wheat flour or the like. Those processes are disclosed in Japanese Patent Kokai 5-301898, 7-48268 and 7-48400. Further, we have found a protein composed of two subunits, each identified as SEQ ID NO:2, and having a very high activity, which is disclosed in Japanese Patent Kokai 7-41499.

BRIEF DESCRIPTION OF THE DRAWING

FIG. 1 is a chromatogram showing the peaks of the fractions obtained by a high performance liquid chromatography of a roughly purified product (mixture) containing plural amylase inhibitors obtained in Example 1.

Our continuing study of the above-mentioned amylase inhibitors led to the elucidation of a new protein composed of two subunits, each identified as SEQ ID NO:1, which can inhibit a human pancreatic α-amylase activity, an increase in blood glucose level and an insulin secretion and an increase in free fatty acid level in blood, thus maintaining a feeling of satiety after meals and easily suppressing appetite. Further, it was found that the new protein was very effective in the treatment or prevention of diabetes and the prevention of obesity, etc.

Thus, the invention provides a new protein composed of two subunits, each identified as SEQ ID NO:1. The new protein has a very high inhibitory activity against the amylase, especially human pancreatic α-amylase. The human pancreatic α-amylase inhibitory activity was found to be 18,000–26,000 U/mg.

The new protein of the invention (SEQ ID NO:1) has a molecular weight of about 25,000 by a gel filtration chromatography using Sephadex G-75. As described in the following Example in detail, the new protein was subjected to a polyacrylamide gel electrophoresis at a gel concentration of 10% (called hereafter "Native-PAGE") according to the method by Davis et al. (Annals New York Academy of Science, 121, pp. 404–427 (1964)) in the same manner as in Japanese Patent Kokai 7-41499, upon which a single band was observed at a mobility of 0.26. Further, a single band was observed at a molecular weight of 12,500 according to SDS polyacrylamide electrophoresis (SDS-PAGE) as explained in detail in the following Examples. This reveals that the new protein is a protein composed of two subunits, each having a molecular weight of 12,500. The electrophoretic mobility and molecular weight of the new protein appear to be approximately identical with the properties of a protein composed of two subunits, each identified as SEQ ID NO:2 (called hereafter "Protein 0.26 AI"), which was previously found out by the present inventors. However, the present new protein is different from Protein 0.26 AI in a retention time when a mixture containing both proteins is subjected to a high performance liquid chromatography, upon which the respective peak fractions appear separately and each fraction is recovered to obtain the proteins individually.

The amino acid sequence of each subunit of the present new protein was determined by a peptide sequencer PSQ-1 (manufactured by Shimadzu Corporation), by which the subunit was found to have a structure of 122 amino acid residues identified as SEQ ID NO:1 (that is, an amino acid sequence wherein 2 amino acid residues at the C-terminal are deleted from Protein 0.26 AI identified as SEQ ID NO:2). Accordingly, the present new protein is a protein constructed of 244 amino acid residues having two subunits, each identified as SEQ ID NO:1. This protein has S—S bonds and is spherical.

The new protein of the present invention (which is called hereafter "Protein (A)" for convenience) has a high inhibitory activity against amylase, especially human pancreatic α-amylase. It has about 5–30 times higher activity as compared with known amylase inhibitors such as a protein composed of two subunits, each identified as SEQ ID NO:4 (called hereafter as "Protein 0.53 AI")(see, Biochim. Biophys. Acta., 743, pp. 52–57 (1983)) or a protein composed of two subunits, each identified as SEQ ID NO:5 (called hereafter "Protein 0.28 AI")(see, Phytochemistry, Vol. 20, No. 8, pp. 1781–1784 (1981)) and also it has somewhat higher activity than a protein composed of two subunits, each identified as SEQ ID NO:3 (called hereafter "Protein 0.19 AI"). That is, it has a high amylase inhibitory activity next to Protein 0.26 AI.

The present Protein (A) includes any protein having an amylase inhibitory activity which is composed of two subunits, each identified as SEQ ID NO:1. The present Protein (A) can be obtained efficiently in an industrial scale by fractionating a mixture composed of plural amylase inhibitors which is produced according to the processes described in Japanese Patent Kokai 5-301898, 7-48268 and 7-48400, by means of a high performance liquid chromatography to the respective amylase inhibitors (proteins).

More specifically, the present Protein (A) can be produced by preparing a mixture composed of amylase inhibitors, for example, according to any of the following processes 1–3, subjecting the mixture to a high performance liquid chromatography using a high pressure linear gradient elution with time/concentration gradient of, for example, Solution I of a 0.1% aqueous solution of trifluoroacetic acid and Solution II of 80% acetonitrile and a 0.1% aqueous solution of trifluoroacetic acid to fractionate the respective amylase inhibitors (proteins) by the differences in retention time, and then recovering the fraction corresponding to Protein (A).

EXAMPLES OF PROCESSES FOR THE PRODUCTION OF THE MIXTURE CONTAINING PROTEIN (A)

1. Process which comprises the steps of:
   (a1) extracting wheat, wheat flour or wheat gluten with water, a dilute acid, a dilute alkali or an aqueous alcohol to obtain a solution containing an amylase inhibitor;
   (b1) adding a polysaccharide to said solution to form an insoluble complex of the amylase inhibitor with the polysaccharide and separating the insoluble complex from the solution;
   (c1) separating the polysaccharide from the complex separated in the above step to collect a solution containing the amylase inhibitor; and
   (d1) treating the collected solution with a cation exchanger to recover the amylase inhibitor from the fractions that have not been adsorbed on the cation exchanger. This process is disclosed in Japanese Patent Kokai 5-301898.

2. Process which comprises the steps of:
   (a2) adding a polysaccharide to either an amylase inhibitor-containing solution extracted from wheat, wheat flour or wheat gluten with water, a dilute acid, a dilute alkali or an aqueous alcohol or an amylase inhibitor-containing waste water washings discharged during the recovery of starch and/or gluten from wheat flour, thereby forming an insoluble complex of the amylase inhibitor with the polysaccharide, and separating the insoluble complex from the solution;
   (b2) separating the polysaccharide from the insoluble complex to collect an amylase inhibitor-containing solution;
   (c2) precipitating 40–70% of the protein in the amylase inhibitor-containing solution to collect the protein thus precipitated and dissolving the collected protein in water to form an amylase inhibitor-containing solution;
   (d2) adding a calcium ion and a phosphate ion to the solution obtained in the above step to form an insoluble complex containing the amylase inhibitor and separating the insoluble complex;
   (e2) solubilizing the amylase inhibitor in water from the insoluble complex separated in the above step to form an amylase inhibitor-containing solution and further including the step to remove impure proteins and other impurities at any stage up to the completion of the above step (c2). This process is disclosed in Japanese Patent Kokai 7-48268.

3. Process which comprises the steps of:
   (a3) treating an amylase inhibitor-containing solution extracted from wheat, wheat flour or wheat gluten with water, a dilute acid, a dilute alkali or an aqueous alcohol, or treating an amylase inhibitor-containing waste water washings discharged during the recovery of starch and/or gluten from wheat flour to modify soluble impure proteins and other impurities contained therein to their insoluble solid forms, and subsequently separating and removing the solid forms;
   (b3) forming an insoluble calcium phosphate gel in the solution obtained in the above step (a3) after removing impurities while adsorbing the amylase inhibitor in said solution on said calcium phosphate gel, and subsequently separating and recovering the calcium phosphate gel containing the amylase inhibitor adsorbed thereon;
   (c3) solubilizing the amylase inhibitor in water from the insoluble calcium phosphate gel containing the adsorbed amylase inhibitor to form a solution containing the amylase inhibitor; and
   (d3) recovering the amylase inhibitor from the solution obtained in the above step (c3). This process is disclosed in Japanese Patent Kokai 7-48400.

In preparing a mixture containing the present Protein (A) according to any of the aforementioned processes 1–3, the present invention can use the operating conditions mentioned in Japanese Patent Kokai 5-301898, 7-48268 and 7-48400, but not limiting thereto.

The new protein of the present invention, Protein A has a very high inhibitory activity against human pancreatic α-amylase, thus inhibiting an increase in blood glucose level, an insulin secretion and an increase in free fatty acid level in blood. Thus, the present Protein (A) can be used effectively as an amylase inhibitor, an for inhibiting an increase in blood glucose level, an agent for controlling an insulin secretion and an agent for suppressing an appetite. When the present Protein (A) is used as an amylase inhibitor, an agent for inhibiting an increase in blood glucose level, an agent for controlling an insulin secretion or an agent for suppressing an appetite, it is preferable for exerting its sufficient effect to use Protein (A) alone in said agents at a content of not less than 20% by weight or in combination with at least one of Proteins 0.26 AI and 0.19 AI at a total content of not less than 20% by weight. In the combined use, the respective proteins may be in any proportion. In that case, Protein (A), Proteins 0.26 AI and 0.19 AI may be either a highly purified product or a roughly purified product.

The amylase inhibitor and the agents for inhibiting an increase in blood glucose level, for controlling an insulin secretion and for suppressing an appetite, which comprise as an active ingredient the present Protein (A), may further contain other components derived from wheat such as proteins, peptides, and starch, dietary fiber, vitamins, minerals, etc. in addition to Protein (A), Proteins 0.26 AI and 0.19 AI.

The amylase inhibitors and the agents of the present invention may be used as such or may be applied in the form of a liquid preparation such as solutions or a solid preparation such as granules or tablets which are formulated with conventional carriers or adjuvants for pharmaceutical preparations. Alternatively, Protein (A), Protein 0.26 AI and/or Protein 0.19 AI may be added to foods, in particular, carbohydrate foods rich in starch such as breads, cookies, noodles, etc., or tea, soup, seasoned fish meal, spreads such as butter or jam.

The amount of Protein (A) or the mixture thereof with Protein 0.26 AI and/or Protein 0.19 AI administered to humans or added to foods may be suitably controlled, depending upon the situation whether or not it may be administered to patients suffering from diabetes or a healthy person or the states or symptoms of the subject to be treated, as well as the type or ingested amount of the foods. The present inhibitors or agents can exert a high level of an amylase inhibitory activity, an inhibitory activity against an increase in blood glucose level, a controlling activity against insulin secretion or an activity maintaining a feeling of satiety at a lower dose. Especially when it is added to foods, it is preferable to control an amount of Protein (A) or a total amount of Protein (A) and Protein 0.26 AI and/or Protein 0.19 AI so as to provide 30–3,000 mg per one meal of ingestive foods.

The agent for inhibiting an increase in blood glucose level, for example, with the content of Protein (A) or the total content of Protein (A), Protein 0.26 AI and/or Protein 0.19 AI being 30% by weight, exhibits an activity of inhibiting an increase in blood glucose level even when administered to a healthy person at a dose of 100 mg per meal. The administration at a unit dose of 250 to 2,500 mg, 3 times a day can very well inhibit an increase in blood glucose level. For diabetic, the administration at a higher dose (usually, about 500–5,000 mg/meal) can effectively inhibit an increase in blood glucose level after meals.

The appetite controlling agent of the invention, for example, with the content of Protein (A) or the total content of Protein (A), Protein 0.26 AI and/or Protein 0.19 AI being 30% by weight, can inhibit appetite by suppressing the feel of hunger with no increase in the content of free fatty acid in blood, when given at a dose of 500 mg to 10 g per meal.

Preferably, the agents of the present invention are formulated into the preparations (e.g., capsules, tablets, granules, powders, pellets, solutions, etc.) so that 100 mg to 10 g, preferably 250 to 5,000 mg of the active ingredient are contained in the agents when administered once. For example, a unit dose of 100 mg to 10 g can achieve sufficient and sure ingestion.

This invention is further illustrated by the following examples, in which the Native-PAGE and SDS-PAGE of Protein (A) were carried out by the following procedure.

In addition, determination of a molecular weight by a gel filtration chromatography using Sephadex G-75, determination of an amino acid sequence of Protein (A), and assay of an inhibitory activity against human pancreatic α-amylase of amylase inhibitors including Protein (A), Protein 0.26 AI, Protein 0.19 AI, Protein 0.53 AI and Protein 0.28 AI were carried out in the following manner.

PROCEDURE FOR NATIVE-PAGE

This was performed by polyacrylamide gel electrophoresis using the gel at a concentration of 10%, in principle, according to the method by Davis et al., Annals New York Academy of Science, 121, pp. 404–427 (1964), as disclosed in Japanese Patent Kokai 7-41499.

(i) Reagents:

The reagents shown in the following Table 1 were prepared and used.

TABLE 1

| Reagents used in Native-PAGE | |
|---|---|
| Solution A: | 1.5M Tris-hydrochloric acid buffer (pH 8.9) |
| Solution B: | 0.5M Tris-hydrochloric acid buffer (pH 6.7) |
| Solution C: | A solution of 29.2 g of acrylamide and 0.8 g of methylenebisacrylamide in a sufficient volume of distilled water to make up a total volume of 100 ml |
| Solution D: | A solution of 10 g of acrylamide and 2.5 g of methylenebisacrylamide in a sufficient volume of distilled water to make up a total volume of 100 ml |
| Solution E: | Riboflavin 4 mg/100 ml |
| Solution F: | 10% Ammonium persulfate |
| Solution for upper electrode: | A mixed solution of 0.025M tris aqueous solution, 0.192M glycine aqueous solution and $1 \times 10^{-6}\%$ Bromophenol Blue |
| Solution for lower electrode: | A mixed solution of 0.025M tris aqueous solution and 0.192M glycine aqueous solution |

(ii) Preparation of separation gel

Native-PAGE was carried out using a slab-type electrophoretic apparatus. A pair of gel molds with a gel thickness of 1 mm was coated with silicone and sealed with a silicone tube so as not to leak a liquid.

4.5 ml of Solution A, 6 ml of Solution C, 7.5 ml of distilled water, 70 µl of Solution F and 10 µl of TEMED (manufactured by Wako Pure Chemical Co., Ltd.) were thoroughly mixed to form a mixed solution.

The sealed gel mold was set up upright and the mixed solution was poured into the gel mold up to about 80% of its height. A small amount of n-butanol was added onto the surface of the solution for accelerating gelation and allowed to stand for a while in such a manner that a mutual contact of the solution surface with air may be avoided, thereby performing gelation.

(iii) Preparation of concentration gel 1 ml of Solution B, 2 ml of Solution D, 4 ml of distilled water, 1 ml of Solution E, 20 µl of Solution F and 10 µl of TEMED were thoroughly mixed to form a mixed solution.

The n-butanol layer was discarded from the separation gel prepared as above, the gel surface was washed with the mixed solution and the mixed solution was further poured into the gel mold so as to fill up the gel mold. A sample comb was inserted into the mold at the upper part thereof and allowed to stand until the solution gelled.

(iv) Electrophoresis

The gel prepared as above was set in an electrophoretic apparatus by removing the silicone tube and the sample comb in the sealed part. The solution for upper electrode was placed in an upper electrolytic cell and the solution for lower electrode was in a lower electrolytic cell, a sample solution having an increased specific gravity by the addition of sucrose was added to each lane and then electrophoresis was carried out at 25 mA until Bromophenol Blue reaches an end of the gel.

(v) Staining and decoloring of gel

After completion of the electrophoresis, the gel was removed from the mold and dipped in a staining solution (0.025% Coomassie Blue R250, 50% methanol and 7% acetic acid) overnight to stain the proteins. After completion of the staining, the gel was dipped in a decoloring solution (7% acetic acid) and allowed to stand while shaking overnight to perform decoloration.

SDS-PAGE

SDS-PAGE was carried out using Phast System (manufactured by Pharmacia).

(i) Preparation of Sample

A sample was treated at 100° C. for 5 min. in a 10 mM tris-hydrochloric acid buffer (pH 8.0) containing 1 mM EDTA, 2.5% SDS, 5% 2-mercaptoethanol and a very small amount of Bromophenol Blue.

(ii) Electrophoresis, Staining and Decoloring

A series of procedures for SDS-PAGE, staining and decoloring were carried out using Phast System. The gel was Phast Gel Homogeneous 20.

DETERMINATION OF MOLECULAR WEIGHT BY GEL FILTRATION CHROMATOGRAPHY USING SEPHADEX G-75

A sample solution was prepared by adding 4 ml of a buffer (20 mM tris, 200 mM NaCl, pH 8.0) to Protein (A) and the sample solution was subjected to a Sephadex G-75 gel filtration column (1.6 cm×90 cm) previously equilibrated with the buffer to perform a gel filtration chromatography at a flow rate of 0.5 ml/min., by which a molecular weight was determined.

DETERMINATION OF AMINO ACID SEQUENCE OF PROTEIN (A)

Protein (A) was pyridylethylated and hydrolyzed with V8 protease, lysylendopeptidase (manufactured by Wako Pure Chemical Industries, Ltd.). The hydrolyzed sample was subjected to HPLC to obtain a hydrolyzed peptide fragment. The resulting peptide fragment was analyzed at the N-terminal of the peptide using a peptide sequencer PSQ-1 (manufactured by Shimadzu Corporation) to determine a whole primary structure. The C-terminal was determined by hydrolyzing with carboxypeptidase and then analyzing a free amino acid thus formed.

DETERMINATION OF INHIBITORY ACTIVITY AGAINST HUMAN PANCREATIC α-AMYLASE

An aqueous sample solution and human pancreatic α-amylase were added to 20 mM piperazine-N,N'-bis(2-ethanesulfonic acid) buffer (pH 6.9) containing 50 mM NaCl, 5 mM $CaCl_2$ and 0.02% egg white albumin. The mixture was allowed to stand at 37° C. for 30 min. and then mixed with 0.5 ml of a 1.5% soluble starch solution (pH 6.9). The resulting solution was allowed to react while maintaining at 37° C. for 10 min. and the reaction was then discontinued by adding 2.5 ml of a quenching solution (0.08M HCl and 0.4M acetic acid). To 0.2 ml of the reaction solution was added 2.5 ml of an iodine solution (0.05% KI and 0.005% iodine), and the mixture was measured for absorbance at 660 nm. In the determination, the amylase was used in an amount sufficient to reduce 80% absorbance when no sample solution was contained therein and the amount of the amylase inhibitor sufficient to inhibit 50% amylase activity was expressed as 1 amylase inhibitory unit (U).

EXAMPLE 1

To 800 kg of wheat flour were added 400 lit. of water and the mixture was kneaded to form a dough. The dough was washed with 6,000 lit. of water to recover 400 kg of gluten and 500 kg of wheat starch. At this stage, 5780 lit. of waste water washings were produced. The pH of waste water washings (aqueous extract) was adjusted to 3 with hydrochloric acid and after allowing to stand for 30 min., adjusted to pH 6.5 with aqueous ammonia, whereby insoluble matters were precipitated. The precipitates were removed to recover 5,200 lit. of a supernatant.

To 1,000 lit. of the supernatant recovered as above were added 300 ppm of sodium alginate. The mixture was adjusted to pH 4.0 and 40 lit. of the gel thus formed were recovered. To the recovered gel was added calcium chloride (dihydrate) so as to give a calcium concentration of 400 ppm, thoroughly stirred and allowed to stand for one hour. Then, the gel was centrifuged by a De Laval centrifuge to recover about 10 lit. of the precipitate. To the precipitate were further added 30 lit. of water to wash the precipitate which was then centrifuged again by a De Laval centrifuge to give 6.5 kg of the precipitate. To the precipitate were added 25 lit. of water and then calcium chloride (dihydrate) so as to give a calcium concentration of 3,000 ppm. The mixture was thoroughly stirred and 25 lit. of the supernatant were recovered by a De Laval centrifuge. On the other hand, 5 lit. of the precipitate separated by a centrifuge were again washed with 12 lit. of an aqueous solution of calcium chloride (3,000 ppm) and the washings were recovered by a De Laval centrifuge. The washings were combined with 25 lit. of the supernatant as obtained previously to give 39 lit. of the eluate.

To 39 lit. of the resultant eluate were added 29.1 g of disodium hydrogenphosphate to adjust pH to 7.2. The resultant solution was heated to 80° C., thermally unstable material was removed by a De Laval centrifuge and the supernatant was concentrated by an ultrafiltration membrane ("NTU-3250 CIR" manufactured by Nitto Denko K. K.), while removing excess calcium salt to give a concentrated solution.

14 lit. of the resultant concentrated solution were adjusted to pH 7.5 with ammonia. After removing impurities by a filter press, the solution was treated with 3 kg of a cation exchange resin ("Diaion HPK-55" manufactured by Mitsubishi Kasei K. K.), and then adjusted to pH 4 with citric acid. The pH-adjusted solution was heat-treated at 80° C. and freeze-dried using freeze-dryer to give about 250 g of dry powders.

1 g of the dry powders was dissolved in 100 ml of a 0.1% aqueous solution of trifluoroacetic acid and fractionated by a high performance liquid chromatography under the operating conditions indicated in the following Table 2 to give the peaks as shown in FIG. 1.

TABLE 2

Operating Conditions for High Performance Liquid Chromatography

Column:

Packing material: CAPCELL PAK C18 SG 120 Å (particle size 3 μm)(manufactured by Shiseido Company, Limited)

Size: 4.6 mmφ×150 mm

Temperature: 50° C.

Flow rate: 0.5 ml/min.

Detection: Absorbance at 280 nm

Mobile phase:

High pressure linear gradient elution with a time/concentration gradient shown below, using Solution A: 0.1% aqueous solution of trifluoroacetic acid, and Solution B: 80% aqueous solution of acetonitrile and 0.1% aqueous solution of trifluoroacetic acid

| Time (min.) | Solution A (%) | Solution B (%) |
| --- | --- | --- |
| 0 | 65.5 | 34.5 |
| 30 | 65.5 | 34.5 |
| 60 | 64.5 | 35.5 |
| 60.1 | 0 | 100 |
| 65.0 | 0 | 100 |

Subsequently, the fraction at peak No. 13 in FIG. 1 was recovered and the recovered fraction was determined for its molecular weight by a gel filtration chromatography using Sephadex G-75 as mentioned above to show that it had a molecular weight of approximately 25,000. Further, this fraction was subjected to SDS-PAGE, upon which a single band was observed at the location corresponding to a molecular weight of 12,500. Accordingly, it was proved that the recovered product from the fraction at peak No. 13 were composed of two subunits, each having a molecular weight of 12,500. The amino acid sequence of the subunit was investigated by the aforementioned method to prove that it is Protein (A) having the structure of 122 amino acid residues identified as SEQ ID NO:1. For reference, the recovered products from the fractions of all other peaks in FIG. 1 were investigated for their molecular weights and amino acid sequences in the same manner as mentioned above. It was proved that the fraction at peak No. 11 was Protein 0.19 AI, the fraction at peak No. 15 was Protein 0.26 AI, the fraction at peak No. 17 was Protein 0.53 AI, and the fraction at peak No. 20 was Protein 0.28 AI.

Protein (A) as recovered above was assayed for its inhibitory activity against human α-pancreatic amylase, with the results as shown in the following Table 3.

Further, known proteins 0.26 AI, 0.19 AI, 0.53 AI and 0.28 AI were assayed for the inhibitory activity against human α-pancreatic amylase in the same manner as mentioned above, with the results shown in the following Table 3.

TABLE 3

| Type of protein | Amylase inhibitory activity (U/mg) |
| --- | --- |
| Protein (A) of the invention (SEQ ID NO:1) | 20,500 |
| Protein 0.26 AI (SEQ ID NO:2) | 26,100 |
| Protein 0.19 AI (SEQ ID NO:3) | 20,300 |
| Protein 0.53 AI (SEQ ID NO:4) | 3,940 |
| Protein 0.28 AI (SEQ ID NO:5) | 840 |

The results in Table 3 show that Protein (A) of the invention has about 5–30 times higher amylase inhibitory activity, as compared with known amylase inhibitors (Proteins 0.53 AI and 0.28 AI), and also that it has a higher activity than Protein 0.19 AI having a high amylase inhibitory activity, thus showing a high amylase inhibitory activity next to Protein 0.26 AI.

EXAMPLE 2

For 10 healthy men not suffering from diabetes, a blood glucose level, an insulin amount in blood and a duration in a feeling of satiety were determined using Protein (A) prepared in Example 1 in a similar manner as described in Example 6 of Japanese Patent Kokai 7-41499. There were obtained substantially similar results as shown in Example 6 of Japanese Patent Kokai 7-41499. Thus, it was proved that Protein (A) of the invention has good effects on the inhibition of an increased blood glucose level and insulin secretion, and on the duration in a feeling of satiety.

What is claimed is:

1. A protein composed of two subunits, each identified as SEQ ID NO:1.

2. The protein of claim 1 having 18,000–26,000 U/mg of human pancreatic α-amylase inhibitory activity.

3. An amylase inhibitor comprising a protein composed of two subunits, each identified as SEQ ID NO:1.

4. The amylase inhibitor of claim 3 wherein it contains not less than 20% by weight of the protein.

5. An amylase inhibitor comprising a protein composed of two subunits, each identified as SEQ ID NO:1, in combination with a protein composed of two subunits, each identified as SEQ ID NO:2 and/or a protein composed of two subunits, each identified as SEQ ID NO:3, the total contents of said proteins being not less than 20% by weight.

6. An agent for inhibiting an increase in blood glucose level which comprises as an active ingredient a protein composed of two subunits, each identified as SEQ ID NO:1.

7. The agent of claim 6 wherein it contains not less than 20% by weight of the protein.

8. An agent for inhibiting an increase in blood glucose level which comprises as an active ingredient a protein composed of two subunits, each identified as SEQ ID NO:1, in combination with a protein composed of two subunits, each identified as SEQ ID NO:2 and/or a protein composed of two subunits, each identified as SEQ ID NO:3, the total contents of said proteins being not less than 20% by weight.

9. An agent for controlling an insulin secretion which comprises as an active ingredient a protein composed of two subunits, each identified as SEQ ID NO:1.

10. The agent of claim 9 wherein it contains not less than 20% by weight of the protein.

11. An agent for controlling an insulin secretion which comprises as an active ingredient a protein composed of two subunits, each identified as SEQ ID NO:1, in combination with a protein composed of two subunits, each identified as SEQ ID NO:2 and/or a protein composed of two subunits, each identified as SEQ ID NO:3, the total contents of said proteins being not less than 20% by weight.

12. An agent for suppressing an appetite which comprises as an active ingredient a protein composed of two subunits, each identified as SEQ ID NO:1.

13. The agent of claim 12 wherein it contains not less than 20% by weight of the protein.

14. An agent for suppressing an appetite which comprises as an active ingredient a protein composed of two subunits, each identified as SEQ ID NO:1, in combination with a protein composed of two subunits, each identified as SEQ ID NO:2 and/or a protein composed of two subunits, each identified as SEQ ID NO:3, the total contents of said proteins being not less than 20% by weight.

15. A food additive comprising a protein composed of two subunits, each identified as SEQ ID NO:1.

16. The food additive of claim 15 wherein it contains not less than 20% by weight of the protein.

17. A food additive comprising a protein composed of two subunits, each identified as SEQ ID NO:1, in combination with a protein composed of two subunits, each identified as SEQ ID NO:2 and/or a protein composed of two subunits, each identified as SEQ ID NO:3, the total contents of said proteins being not less than 20% by weight.

* * * * *